United States Patent [19]

Kita et al.

[11] 4,316,960

[45] Feb. 23, 1982

[54] PREPARATION OF 2,5-DIKETOGLUCONIC ACID

[75] Inventors: Donald A. Kita, Essex; Dennis M. Fenton, Gales Ferry, both of Conn.

[73] Assignee: Pfizer Inc., New York, N.Y.

[21] Appl. No.: 139,036

[22] Filed: Apr. 10, 1980

Related U.S. Application Data

[63] Continuation-in-part of Ser. No. 79,665, Sep. 28, 1979, abandoned.

[51] Int. Cl.³ .................................................. C12P 7/58
[52] U.S. Cl. .................................................. 435/137
[58] Field of Search .............................. 435/138, 137

[56] References Cited

U.S. PATENT DOCUMENTS

| | | | |
|---|---|---|---|
| 3,234,105 | 2/1966 | Motizuki et al. | 435/138 |
| 3,790,444 | 2/1974 | Oga et al. | 435/137 |
| 3,998,697 | 12/1976 | Sonoyama et al. | 435/138 |

OTHER PUBLICATIONS

Product Bulletin, CPC International Inc. ARGO TM Steepwater E801.

*Primary Examiner*—Alvin E. Tanenholtz
*Attorney, Agent, or Firm*—Charles J. Knuth; Peter C. Richardson

[57] ABSTRACT

A process for the preparation of 2,5-diketogluconic acid by the aerobic propagation of *Acetobacter cerinus* in a fermentation medium containing above about 20 and up to about 30% (wt/vol) glucose and at least about 0.04 wt. % choline based on the amount of glucose in the medium.

9 Claims, No Drawings

PREPARATION OF 2,5-DIKETOGLUCONIC ACID

CROSS-REFERENCE TO RELATED APPLICATION

This application is a continuation-in-part of copending U.S. application Ser. No. 79,665 filed Sept. 28, 1979, now abandoned.

BACKGROUND OF THE INVENTION

This invention relates to the preparation of 2,5-diketogluconic acid, which is useful as an intermediate for the preparation of ascorbic acid. A solution of 2,5-diketogluconic acid may be selectively reduced to 2-ketogulonic acid, which may be converted to ascorbic acid. The reduction of 2,5-diketogluconic acid may be effected by reduction with an alkali metal borohydride, as disclosed in U.S. Pat. No. 4,159,990 or by a fermentive reduction as described, for example, in U.S. Pat. Nos. 3,922,194, 3,959,076 and 3,963,574.

2,5-Diketogluconic acid is also useful as an intermediate for the preparation of comenic acid by heating in the presence of an acid, as described, for example, in U.S. Pat. No. 3,654,316.

Heretofore, 2,5-diketogluconic acid has been produced by several different varieties of bacteria such as *Acetobacter melanogenum, Acetobacter aurantium, Gluconoacetobacter rubiginosus, Gluconoacetobacter liquifaciens* and *Pseudomonas sesami*. The use of these microorganisms, however, is not satisfactory from an industrial point of view because of relatively low yields of 2,5-diketogluconic acid, relatively long fermentation times and because of the production of large amounts of brown or yellow-brown pigments as by-products of cultivation, thereby decreasing the purity of the desired 2,5-diketogluconic acid.

U.S. Pat. No. 3,790,444 relates to the production of 2,5-diketogluconic acid, without accompanying brown pigment, by a new species designated *Acetobacter fragum* ATCC No. 21409.

U.S. Pat. application Ser. No. 79,668 filed Sept. 28, 1979 now U.S. Pat. No. 4,263,402 relates to the preparation of 2,5-diketogluconic acid in good yields without the formation of pigmented material by the aerobic propagation of *Acetobacter cerinus* in a glucose containing medium. While total amounts of glucose from about 2.5% to about 20% (wt/vol) can be utilized, it has been found that initial glucose concentrations in the medium greater than about 15% cannot be tolerated by the microorganisms. Accordingly, total amounts of glucose greater than about 15% (wt/vol) can only be utilized by conducting the fermentation at an initial glucose concentration of about 10% to 15% (wt/vol) and thereafter adding further increments of glucose to the fermentation medium during the course of the fermentation, the concentration of glucose in the medium not exceeding about 15% (wt/vol) at any given time. Accordingly, heretofore the overall concentrations, or production capacities, of 2,5-diketogluconic acid have been limited by the relatively low initial glucose concentration that can be employed in the fermentation medium. The productivity of processes employing other microorganisms for the preparation of 2,5-diketogluconic acid, as described hereinabove, is also limited by the necessity of using relatively low initial glucose concentration in the fermentation medium.

It will be readily apparent that a process wherein initial glucose concentrations higher than about 15% (wt/vol), especially levels above 20%, can be tolerated and utilized by the microorganisms for the preparation of 2,5-diketogluconic acid will provide a substantial increase in production capacity and will result in substantial economies of operation. Such a process also avoids the possibility of contamination of the fermentation medium that may occur when production capacities are increased by adding further increments of glucose during the course of the fermentation.

SUMMARY OF THE INVENTION

In accord with the present invention, it has now been found that initial glucose concentrations above 20% and up to about 30% (wt/vol) in a fermentation medium can be utilized by the microorganism *Acetobacter cerinus* for the production of 2,5-diketogluconic acid when at least about 0.04 wt. % of choline, based on the amount of D-glucose in the medium, is added to the fermentation medium. More particularly, the present invention provides a process for the production of 2,5-diketogluconic acid in high concentrations in the fermentation medium by aerobically propagating *Acetobacter cerinus* in a fermentation medium containing D-glucose in an initial concentration above about 20% and up to about 30% (wt/vol) and choline in an amount of at least about 0.04 wt. % based on the amount D-glucose in the medium. The initial glucose concentration in the fermentation medium is preferably about 25% to 30% (wt/vol). The propagation is preferably conducted at a temperature of 25° to 30° C., preferably at a pH from about 5 to 6. Preferred strains are *Acetobacter cerinus* or *Acetobacter cerinus* IFO 3263 and IFO 3266.

DETAILED DESCRIPTION OF THE INVENTION 2,5-Diketogluconic acid is prepared in the process of the present invention in good yields without the formation of significant amounts of pigmented materials and in relatively short fermentation times. A number of strains of *Acetobacter cerinus*, including IFO 3262 (ATCC 12303), IFO 3263, IFO 3264, IFO 3265, IFO 3266, IFO 3267, IFO 3268 and IFO 3269 are publicly available and can be used in the present process for making 2,5-diketogluconic acid. Particularly preferred strains are IFO 3263 and IFO 3266. It will be understood that mutants of these microorganisms produced by conventional methods, for example by irradiation with X-rays or ultra-violet light, treatment with nitrogen mustards or the like, will also be useful in the present process and are embraced by the specification and claims hereof.

The *Acetobacter cerinus* is cultivated in a medium of which the main carbon source is D-glucose. It will be understood that, in accord with conventional fermentation practice, the fermentation medium will also contain sources of nitrogen, potassium, phosphorus and magnesium. The term "fermentation medium" in the specification and claims hereof is intended to define a medium containing such compounds. When employing the *Acetobacter cerinus* microorganisms in the present process, it is not necessary to use expensive organic nitrogen sources such as peptone or meat extract. The nitrogen can be economically provided by the use of urea or inorganic nitrogen sources, such as ammonium sulfate, ammonium nitrate, ammonium phosphate or similar salts, generally in amounts from between about 0.1 gram to 2 grams per liter of fermentation medium, when nicotinic acid is also added as a growth factor, generally in an amount of about 0.2 to 10 mg per liter of fermentation medium. The potassium, magnesium and phosphorus are readily provided by the addition of salts such as potassium phosphate, ammonium phosphate, magnesium sulfate or similar salts, generally in amounts of about 0.1 to about 1 gram per liter of fermentation medium. Considerable variation in the composition of the fermentation medium is, however, possible. Other suitable media will be readily apparent to those skilled in the art and the present process is not intended to be limited to the use of the particular media described above and in the examples hereof. In accord with the present process, the fermentation medium contains D-glucose in initial concentrations higher than has previously been possible without deleterious effect on the microorganisms employed in the fermentation. Specifically, the initial D-glucose concentration in the fermentation medium employed in the present process is in the range above about 20% and up to about 30% (wt/vol), especially from about 25% to 30% (wt/vol). If desired, D-glucose can be added as cerelose (D-glucose monohydrate).

In order for the *Acetobacter cerinus microorganisms to be able to tolerate and utilize such high glucose concentrations in the fermentation medium, it is necessary to add choline to the fermentation medium in an amount of at least about* 0.04 wt. % based on the initial amount of D-glucose in the fermentation medium. If desired, relatively high levels of choline, for example about 0.5 wt. % based on the initial D-glucose concentration in the fermentation medium, can be employed, although there is little advantage in using more than about 0.1 wt. % choline, and from about 0.04 to about 0.06 wt. % choline is generally preferred. Choline may be added either as the free base or as a salt, for example, as choline chloride, choline bicarbonate, choline citrate, choline gluconate or similar salts. Choline chloride is a preferred salt. The concentration of choline as defined in the specification and claims hereof is calculated as choline base. A small part of the necessary choline may be provided, if desired, by the addition of corn steep liquor to the fermentation medium. Corn steep liquor, which has been used in fermentation media as a source of vitamins and minerals, generally contains only about 0.5 to 3 mg of choline per gram of corn steep liquor. However, no more than about 5 grams of corn steep liquor per liter of fermentation medium will ordinarily be employed since corn steep liquor contains color bodies and the addition of more than about 5 grams of corn steep liquor per liter of fermentation medium makes recovery and purification of the 2,5-diketogluconic acid more difficult. Accordingly, corn steep liquor can only be used, if desired, as a source of a small part of the choline necessary for the fermentation and the remainder of the required amount of choline is added to the fermentation medium as choline base or a salt thereof, as described above.

The fermentation is generally conducted at a temperature from about 20° C. to 35° C., preferably between 25° C. and 30° C., most preferably around 28° C. The initial pH of a culture medium will range from about 3.5 to 7.5, preferably from about 5 to 6. During the course of the fermentation the pH is desirably maintained in this range, preferably at about 5.5, for example by the addition of an alkali metal hydroxide, preferably sodium hydroxide solution. Alternatively, an alkali metal or alkaline earth metal carbonate, preferably calcium carbonate may be used for pH control and is added for this purpose in medium makeup after autoclaving in an amount sufficient to give the desired pH, generally about 20 to 30 grams per 100 grams of glucose. It will be understood that the 2,5-diketogluconic acid will be produced in such fermentation media in the form of the corresponding alkali or alkaline earth metal salts, such as the sodium or calcium salts, and that such salts are embraced by the use of the term "2,5-diketogluconic acid" in the specification and claims hereof.

After inoculation, the fermentation medium is agitated, for example with a mechanical stirrer, and aerated, preferably at a rate of about 0.5 to 1 volume of air per volume of fermentation broth per minute. If desired, additional glucose can be added during the fermentation to replace some of the glucose utilized in the fermentation, thereby increasing the overall concentration of 2,5-diketogluconic acid obtained in the fermentation broth.

The fermentation is continued until the desired yield is obtained. For example, employing *Acetobacter cerinus* IFO 3263 or 3266 a fermentation time of about 40 to 50 hours will give a yield of about 90 to 95% 2,5-diketogluconic acid, based on D-glucose. However, some variation in reaction times and yields are to be expected depending on the particular strain of microorganism, the glucose concentration in the fermentation medium and the cultivation temperature.

While not wishing to be bound by the following mechanism, it is believed that the conversion of glucose to 2,5-diketogluconic acid proceeds by the following pathways:

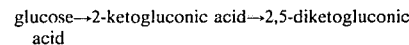

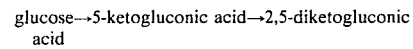

The intermediate 2-ketogluconic and 5-ketogluconic acids and 2,5-diketogluconic acid may be separated by paper chromatography using Whatman No. 1 and No. 4 paper and a solvent system of methyl ethyl ketone:acetone:formic acid:water (80:6:2:12). The acids spots are located by spraying with a 0.2% o-phenylenediamine ethanolic solution containing 1% nitric acid and heating to about 70° C. (5-ketogluconic acid - blue; 2-ketogluconic acid - yellow; 2,5-diketogluconic acid - green). High pressure liquid chromatography may also be used. Using the above methods, the progress of the fermentation can be followed.

2,5-Diketogluconic acid may be separated and recovered from the final fermentation broth by any conventional procedures known to those skilled in the art. For example the fermentation broth may be filtered, the pH of the aqueous filtrate adjusted to about 2 to 2.5 by addition of a mineral acid such as hydrochloric acid, followed by concentration of the solution and addition of a lower alkyl alcohol, preferably ethanol or methanol. On standing, 2,5-diketogluconic acid in the form of its calcium or sodium salt separates from solution as a solid. The 2,5-diketogluconic acid may be obtained from the salt by treatment with a dilute mineral acid, followed for example, by treatment with a cation exchange resin such as a sulfonic acid resin, for example, Dowex 50 (Dow Chemical Company).

If desired, the fermentation broth may be processed to convert the formed 2,5-diketogluconic acid to other desired products, for example, by fermentive reduction to 2-ketogulonic acid as described in U.S. Pat. Nos. 3,922,194, 3,959,076 or 3,963,574. Alternatively, the filtered fermentation broth may be used as a suitable reaction solution for the reduction of 2,5-diketogluconic acid to a 2-ketogulonic acid-containing solution by reaction with an alkali metal borohydride as described in U.S. Pat. No. 4,159,990. The 2-ketogulonic acid produced in these reactions is readily converted to ascorbic acid by means known in the art, for example by heating the methyl ester thereof in the presence of a base.

The present invention is illustrated by the following examples. However it should be understood that the invention is not limited to the specific details of these examples.

EXAMPLE 1

The following aqueous inoculum medium was prepared:

| Ingredient | Grams/liter |
| --- | --- |
| Glucose monohydrate | 25 |
| Corn steep liquor | 5 |
| KH$_2$PO$_4$ | 0.5 |
| K$_2$HPO$_4$ | 0.5 |
| MgSO$_4$ . 7H$_2$O | 0.2 |
| CaCO$_3$ | 7.0 |
| pH 6.2 | |

A shake flask containing one liter of medium was autoclaved for 30 minutes at 121° C. Cells of *Acetobacter cerinus* IFO 3263 from a nutrient agar slant (5 ml of a 20 ml sterile aqueous suspension) were added to the flask, which was then shaken on a rotary shaker at about 28° C. for about 24 hours. The pH of the cooled medium was 5.0.

An aliquot of the culture growth sufficient to provide a 10% v/v inoculum was added to a 4-liter stirred fermentor containing 2 liters of the following production medium:

| Ingredient | | |
| --- | --- | --- |
| Glucose monohydrate | 225 | g/l |
| Corn steep liquor | 0.5 | g/l |
| (NH$_4$)$_2$HPO$_4$ | 0.5 | g/l |
| KH$_2$PO$_4$ | 1.5 | g/l |
| MgSO$_4$ . 7H$_2$O | 0.5 | g/l |
| Urea | 1.0 | g/l |
| Choline Chloride | 100 | mg/l |
| Nicotinic acid | 10 | mg/l |
| CuSO$_4$ . 5H$_2$O | 2.0 | mg/l |
| P-2000 Antifoam | 1.0 | mg/l |
| pH 6.0 | | |

The fermentation was conducted at 28° C. with stirring at 1700 rpm and aeration at a rate of 1.0 volume per volume of broth per minute. The pH was maintained at 5.5 by addition of a 20% sodium hydroxide solution as required. 2,5-Diketogluconic acid as the sodium salt was obtained in a yield of 95% after a fermentation time of 48 hours.

EXAMPLE 2

The following aqueous inoculum medium was prepared:

| Ingredient | Grams/liter |
| --- | --- |
| Glucose Monohydrate | 25 |
| Corn Steep Liquor | 5 |
| KH$_2$PO$_4$ | 0.5 |
| K$_2$HPO$_4$ | 0.5 |
| MgSO$_4$ . 7H$_2$O | 0.2 |
| CaCO$_3$ | 7.0 |

A shake flask containing one liter of medium was autoclaved for 30 minutes at 121° C. Cells of *Acetobacter cerinus* IFO 3263 from a nutrient agar slant (5 ml of a 20 ml sterile aqueous suspension) were added to the flask, which was then shaken on a rotary shaker at about 28° C. for about 24 hours. The pH of the cooled medium was 5.0.

An aliquot of the culture growth sufficient to provide a 10% v/v inoculum was added to a 4-liter stirred fermentor containing 2 liters of the following medium:

| Second Stage Inoculum | Grams/Liter | |
| --- | --- | --- |
| Glucose Monohydrate | 100 | |
| Corn Steep Liquor | 0.5 | |
| (NH$_4$)$_2$HPO$_4$ | 0.5 | |
| KH$_2$PO$_4$ | 1.5 | |
| MgSO$_4$ . 7H$_2$O | 0.5 | |
| Urea | 1.0 | |
| Nicotinic Acid | 10 | mg |
| CuSO$_4$ . 5H$_2$O | 2.0 | mg |
| Choline Chloride | 500 | mg |
| P2000 | 0.5 | ml |

The second stage was conducted at 28° C. with stirring at 1700 rpm and aeration at a rate of 1.0 volume per volume of broth per minute. The pH was maintained at 5.5 by addition of a 20% sodium hydroxide solution as required.

After 20 hours an aliquot of the culture growth sufficient to provide a 10% v/v inoculum was added to a 14-liter stirred fermentor containing 6 liters of the following production medium:

| Ingredient | Grams/liter | |
| --- | --- | --- |
| Glucose Monohydrate | 334 | |
| Corn Steep Liquor | 0.5 | |
| (NH$_4$)$_2$HPO$_4$ | 0.58 | |
| KH$_2$PO$_4$ | 1.5 | |
| MgSO$_4$ . 7H$_2$O | 0.5 | |
| Urea | 1.0 | |
| Nicotinic Acid | 10.0 | mg |
| CuSO$_4$ . 5H$_2$O | 2.0 | mg |
| Choline Chloride | 150 | mg |
| P2000 | 0.5 | ml |

The fermentation was conducted at 28° C. with stirring at 750 rpm and aeration at a rate of 1.0 volume per volume of broth per minute. The pH was maintained at 5.5 by addition of a 20% sodium hydroxide solution as required. 2,5-Diketogluconic acid as the sodium salt was obtained in a yield of 95% after a fermentation time of 65-70 hours.

EXAMPLE 3

Following the procedure of Example 1, *Acetobacter cerinus* strains IFO 3262, 3264, 3265, 3266, 3267, 3268 and 3269 were each tested. In each case, the fermentation product contained 2,5-diketogluconic acid in greater than 50% yield, together with some unconverted 2-ketogluconic acid and 5-ketogluconic acid intermediates. Higher yields of the desired 2,5-diketogluconic acid may be obtained by using longer fermentation times when employing these strains of *Acetobacter cerinus*.

We claim:

1. A process for the production of 2,5-diketogluconic acid which comprises aerobically propagating *Acetobacter cerinus* in a fermentation medium containing D-glucose in an initial concentration of above about 20% and up to about 30% (wt/vol) and choline in an amount of at least about 0.04 wt. % based on the initial amount of D-glucose in said medium.

2. A process according to claim 1 wherein said initial concentration of D-glucose is from about 25% to 30% (wt/vol).

3. A process according to claim 1 wherein said medium contains choline in an amount between about 0.04 wt. % and 0.1 wt. %.

4. A process according to claim 1 wherein said propagation is at a temperature between about 25° C. and 30° C.

5. A process according to claim 1 wherein said propagation is at a pH from about 5 to 6.

6. A process according to claim 5 wherein said pH is maintained by the addition of sodium hydroxide.

7. A process according to claim 1 wherein said medium contains choline in an amount between about 0.04 wt. % and 0.1 wt. % and said propagation is at a temperature between about 25° C. and 30° C. and a pH from about 5 to 6.

8. A process according to claim 1 or claim 7 wherein said *Acetobacter cerinus* is strain IFO 3263.

9. A process according to claim 1 or claim 7 wherein said *Acetobacter cerinus* is strain IFO 3266.

* * * * *